United States Patent
Lee et al.

(10) Patent No.: US 10,071,084 B2
(45) Date of Patent: Sep. 11, 2018

(54) NANOPARTICLE, METHOD OF PREPARATING THE SAME, AND USE OF THE NANOPARTICLE

(71) Applicant: Samsung Electronics Co., Ltd., Suwon-si, Gyeonggi-do (KR)

(72) Inventors: Don-wook Lee, Seoul (KR); Jung-yong Nam, Incheon (KR); Hyun-ryoung Kim, Guri-si (KR); Eun-sung Park, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 60 days.

(21) Appl. No.: 14/472,722

(22) Filed: Aug. 29, 2014

(65) Prior Publication Data

US 2015/0118289 A1  Apr. 30, 2015

(30) Foreign Application Priority Data

Oct. 24, 2013  (KR) ........................ 10-2013-0127298

(51) Int. Cl.
| | | |
|---|---|---|
| *A61K 31/00* | (2006.01) | |
| *A61K 31/4412* | (2006.01) | |
| *A61K 9/127* | (2006.01) | |
| *A61K 9/51* | (2006.01) | |
| *A61K 31/436* | (2006.01) | |
| *A61K 31/337* | (2006.01) | |
| *A61K 31/44* | (2006.01) | |
| *A61K 31/506* | (2006.01) | |
| *A61K 31/704* | (2006.01) | |
| *A61K 31/7048* | (2006.01) | |

(52) U.S. Cl.
CPC ........ *A61K 31/4412* (2013.01); *A61K 9/1271* (2013.01); *A61K 9/5169* (2013.01); *A61K 31/337* (2013.01); *A61K 31/436* (2013.01); *A61K 31/44* (2013.01); *A61K 31/506* (2013.01); *A61K 31/704* (2013.01); *A61K 31/7048* (2013.01)

(58) Field of Classification Search
None
See application file for complete search history.

(56) References Cited

U.S. PATENT DOCUMENTS

| | | |
|---|---|---|
| 5,683,715 A | 11/1997 | Boni et al. |
| 5,916,596 A | 6/1999 | Desai et al. |
| 6,200,598 B1 | 3/2001 | Needham |
| 6,749,868 B1 | 6/2004 | Desai et al. |
| 7,672,704 B2 | 3/2010 | Viglianti et al. |
| 7,769,423 B2 | 8/2010 | Viglianti et al. |
| 7,901,709 B2 | 3/2011 | Needham |
| 2007/0207194 A1 | 9/2007 | Grayburn et al. |
| 2008/0213374 A1 | 9/2008 | Carty et al. |
| 2009/0098212 A1 | 4/2009 | Fossheim et al. |
| 2009/0246127 A1 | 10/2009 | Hummel et al. |
| 2010/0166872 A1 | 7/2010 | Singh et al. |
| 2010/0209353 A1* | 8/2010 | Kwon .................. A61K 9/5123 424/9.6 |
| 2011/0177009 A1 | 7/2011 | Langereis et al. |
| 2011/0200665 A1 | 8/2011 | Mei et al. |
| 2012/0121695 A1 | 5/2012 | Lauten et al. |
| 2016/0151325 A1* | 6/2016 | Desai .................. A61K 9/1075 424/491 |

FOREIGN PATENT DOCUMENTS

| | | |
|---|---|---|
| EP | 0395765 A1 | 11/1990 |
| KR | 1020130042905 A | 4/2013 |

OTHER PUBLICATIONS

Full Prescribing Information for Abraxane; Updated on Oct. 12, 2012 (PDF downloaded from www).*
Perche et al., Recent Trends in Multifunctional Liposomal Nanocarriers for Enhanced Tumor Targeting, Journal of Drug Delivery, 2013: article ID 705265,1-32 (2013).
Ibrahim et al., "Phase I and Pharmacokinetic Study of ABI-007, a Cremophor-free, Protein-stabilized, Nanoparticle Formulation of Paclitaxel[1]", *Clinical Cancer Research*, vol. 8, pp. 1038-1044 (2002).
Ibrahim et al., "Assessment Report for Abraxane", *European Medicines Agency* Doc. Ref: EMEA/47053/2008 (2008).

* cited by examiner

*Primary Examiner* — Anand U Desai
(74) *Attorney, Agent, or Firm* — Leydig, Voit & Mayer, Ltd.

(57) ABSTRACT

A nanoparticle including a hydrophobic active ingredient and a polypeptide, as well as a liposome including the nanoparticle and methods of making and using the nanoparticle.

18 Claims, 7 Drawing Sheets

NANOPARTICLE, METHOD OF PREPARATING THE SAME, AND USE OF THE NANOPARTICLE

RELATED APPLICATION

This application claims the benefit of Korean Patent Application No. 10-2013-0127298, filed on Oct. 24, 2013, in the Korean Intellectual Property Office, the disclosure of which is incorporated herein in its entirety by reference.

BACKGROUND

1. Field

The present disclosure relates to nanoparticles including hydrophobic active ingredients and polypeptides, methods of preparing the nanoparticles, and use of the nanoparticles.

2. Description of the Related Art

Hydrophobic drugs may be delivered by various methods, for example, using emulsionss, co-solvents, or micelles. In the case of liposomes, hydrophobic drugs may be encapsulated within a lipid bilayer, and may affect properties of the lipid bilayer, such as stability or stimulus-sensitivity. In addition, the hydrophobic drugs may not be efficiently released due to strong coherence between the hydrophobic drugs and the lipid bilayer.

Meanwhile, there has been research on albumin as a carrier for hydrophobic drugs since albumin has a hydrophobic pocket that may strongly bind to hydrophobic drugs. However, since it may be difficult to target diseased tissues when albumin is used as a drug carrier, there may be side-effects on normal tissues.

Therefore, a nanoparticle including a hydrophobic drug and albumin may be prepared, wherein albumin is used as a drug carrier. However, when a hydrophobic drug is mixed with various types of chemical additives and milled to be formulated as a nanoparticle, problems may result. For example, the nanoparticle may be toxic due to the use of chemical additives, the nanoparticle preparation method may be complicated, or the nanoparticle may not have stimulus sensitivity. Similarly, when a nanoparticle including a hydrophobic drug and albumin are prepared by using a high-pressure homogenizer under high shear conditions, the nanoparticle preparation method may be complicated and the nanoparticle may not have temperature sensitivity.

Therefore, there is a demand for simple methods of preparing a nanoparticle including a hydrophobic drug and albumin, and methods of controlling the nanoparticle to release the hydrophobic drug at a target site in the body of a subject.

SUMMARY

Provided is a nanoparticle comprising a hydrophobic active ingredient and a polypeptide, wherein the molar ratio of the hydrophobic active ingredient to the polypeptide is about 0.01:1 to about 100:1.

Also provided is a method for manufacturing the nanoparticle by incubating a hydrophobic active ingredient and a polypeptide to prepare the nanoparticle.

Further provided is a liposome including the nanoparticle and a lipid bilayer, and a pharmaceutical composition including the liposomes.

Also provided is a method of delivering a hydrophobic active ingredient to a target site in the body of a subject by administering the liposome containing the nanoparticle to the subject, and applying a stimulus to the target site, whereupon the stimulus reaches the liposome at the target site and causes the liposome to release the nanoparticle.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
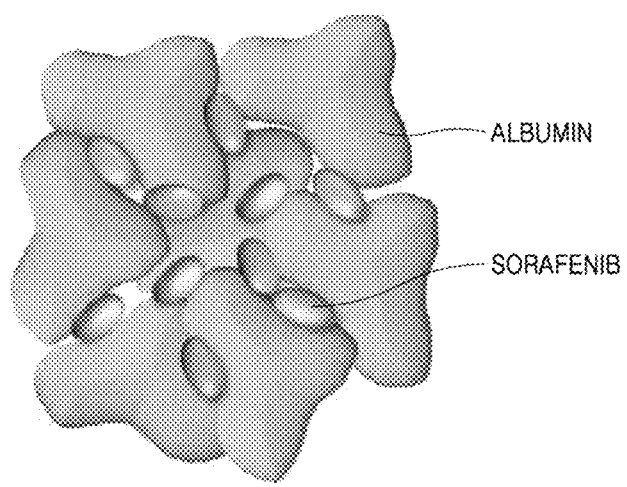
FIG. 1A is a schematic diagram illustrating a nanoparticle including sorafenib (SRF) and bovine serum albumin (BSA).

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

According to an aspect of the present invention, a nanoparticle includes a hydrophobic active ingredient and a polypeptide, wherein the hydrophobic active ingredient is present with respect to the polypeptide at a molar ratio ranging from about 0.01 to about 100.

The term "hydrophobic" as used herein refers to properties that a material does not easily combine with a water molecule or does not easily dissolve in water, or refers to non-polar properties of the material. The term "hydrophobic" as used herein may be used interchangeably with the term "lipophilic." Hydrophobic materials may be classified according to water solubility thereof. For example, a hydrophobic material that is water soluble in a range of about 1 mg/ml to about 10 mg/ml is slightly soluble, a hydrophobic material that is water soluble in a range of about 0.1 mg/ml to about 1 mg/ml is very slightly soluble, and a hydrophobic material that is water soluble at a level of about 0.1 mg/ml or less is substantially insoluble. All solubility assumes standard conditions (25° C. and 1 atm) unless otherwise stated.

The term "active ingredient" as used herein refers to a biologically active material, and examples thereof include a compound (e.g., small organic molecule, "small" in this context referring generally to molecules other than polypeptides, proteins, and nucleic acids), a protein, a peptide, a nucleic acid, a nanoparticle, or any combination thereof. Examples of the active ingredient include an anticancer drug, an anti-angiogenesis inhibitor, an anti-inflammatory drug, an analgesic, an antarthritic, a sedative, an antidepressant, an antipsychotic, a tranquilizer, an antianxiety drug, a narcotic antagonist, an anti-Parkinson's disease drug, a cholinergic agent, an immunosuppressive agent, an antiviral agent, an antibiotic, an appetite suppressant, an anticholinergic, an antihistamine, an anti-migraine drug, a hormone, a vasodilator, a birth control drug, an antithrombotic agent, a diuretic, an antihypertensive, a cardiovascular drug, a wrinkle-diminishing agent, an inhibitor of skin aging, a skin whitening agent, or any combination thereof.

The hydrophobic active ingredient may be a hydrophobic drug, an imaging agent, or any combination thereof. The hydrophobic active ingredient may include a chemical material or a bio-drug with a water solubility of 10 mg/ml or less. For example, the hydrophobic active ingredient may be an anthracycline-based material, a hydrophobic glucocorticoid, a steroid-based material, a taxane-based drug, a cyclic peptide-based drug, or any combination thereof. The anthracycline-based material may be doxorubicin, daunorubicin, epirubicin, idarubicin, valrubicin, mitoxantrone, or any combination thereof. The hydrophobic glucocorticoid may be dexamethasone, trimacinolone, beclomethasone diproprionate, trimacinolone acetonide, trimacinolone diacetate, bethamethasone diproprionate, testosterone, budesonide, 17α-ethinylestradiol, levonorgestrel, fluticasone proprionate, or any combination thereof. For example, the hydrophobic active ingredient may be a liposome including sorafenib, paclitaxel, docetaxel, doxorubicin, cyclosporine A, amphothericin B, indinavir, rapamycin, coenzyme Q10, ursodeoxycholic acid, ilaprazole, imatinib mesilate, tanespimycin, or any combination thereof. The imaging agent or contrast media refers to a material to enhance contrast of an image that shows tissues or blood vessels clearly at the time of examination such as magnetic resonance imaging (MRI) and computed tomography (CT) by artificially increasing X-ray absorption differences of each tissue. The imaging agent may be a transitional element or a chelate complex of the transitional element.

The polypeptide may be a polypeptide that binds to a hydrophobic active ingredient. The polypeptide may be, for example, albumin, transferrin, apolipoprotein, a fragment thereof, or any combination thereof. The albumin may be serum albumin, and the serum albumin may be human serum albumin (HSA) or bovine serum albumin (BSA). The transferrin is an iron-binding glycoprotein. The apolipoprotein may be apolipoprotein A, apolipoprotein B, apolipoprotein C, apolipoprotein D, apolipoprotein E, or apolipoprotein H.

The term "nanoparticle" as used herein refers to a particle of which one or more dimensions is in a range of about 1 nm to about 100 nm. The nanoparticle as a drug carrier may have a structure of, for example, a conjugate of a polymer and a drug, a polymer micelle, a dendrimer, a liposome, or a nanotube.

The molar ratio of the hydrophobic active ingredient to the polypeptide in the nanoparticle may be in a range of about 0.01:1 to about 100:1, about 0.01:1 to about 90:1, about 0.01:1 to about 80:1, about 0.01:1 to about 70:1, about 0.01:1 to about 60:1, about 0.01:1 to about 50:1, about 0.01:1 to about 40:1, about 0.01:1 to about 30:1, about 0.01:1 to about 20:1, about 0.01:1 to about 10:1, about 0.05:1 to about 10:1, about 0.1:1 to about 10:1, about 0.15:1 to about 10:1, about 0.2:1 to about 10:1, about 0.25:1 to about 10:1, about 0.3:1 to about 10:1, about 0.35:1 to about 10:1, about 0.4:1 to about 10:1, about 0.45:1 to about 10:1, about 0.5:1 to about 10:1, about 0.5:1 to about 9.5:1, about 0.5:1 to about 9:1, about 0.5:1 to about 8.5:1, about 0.5:1 to about 8:1, about 0.5:1 to about 7.5:1, about 0.5:1 to about 6.5:1, or about 0.5:1 to about 6:1.

The average diameter of the nanoparticle may be in a range of about 10 nm to about 500 nm, about 10 nm to about 480 nm, about 10 nm to about 460 nm, about 10 nm to about 440 nm, about 10 nm to about 420 nm, about 10 nm to about 400 nm, about 10 nm to about 380 nm, about 10 nm to about 360 nm, about 10 nm to about 340 nm, about 10 nm to about 320 nm, about 10 nm to about 300 nm, about 15 nm to about 300 nm, about 20 nm to about 300 nm, about 25 nm to about 300 nm, about 30 nm to about 300 nm, about 35 nm to about 280 nm, about 40 nm to about 260 nm, about 45 nm to about 240 nm, about 50 nm to about 220 nm, about 55 nm to about 200 nm, about 60 nm to about 180 nm, about 65 nm to about 160 nm, about 70 nm to about 140 nm, about 75 nm to about 120 nm, about 80 nm to about 115 nm, about 85 nm to about 110 nm, about 90 nm to about 105 nm, or about 95 nm to about 100 nm.

According to another aspect of the present invention, a method of preparing a nanoparticle includes incubating a hydrophobic active ingredient and a polypeptide to prepare a nanoparticle, wherein the nanoparticle comprises the hydrophobic active ingredient and the polypeptide, and the hydrophobic active ingredient is contained at a molar ratio in a range of about 0.01:1 to about 100:1 with respect to the polypeptide.

Detailed descriptions of the term hydrophobic, the hydrophobic active ingredient, the polypeptide, the nanoparticle, and the molar ratio of the hydrophobic active ingredient with respect to the polypeptide have already been described.

The incubating of the hydrophobic active ingredient and the polypeptide may be performed in vitro. The incubating of the hydrophobic active ingredient and the polypeptide may be performed at a temperature, for example, in a range of about 0° C. to about 50° C., about 0° C. to about 45° C., about 0° C. to about 40° C., about 0° C. to about 35° C., about 0° C. to about 30° C., about 0° C. to about 25° C., about 5° C. to about 25° C., about 10° C. to about 25° C., about 15° C. to about 25° C., or at room temperature. For example, the incubating of the hydrophobic active ingredient and the polypeptide may be performed by processes of rotating, vortexing, stirring, or any combination thereof.

The hydrophobic active ingredient and the polypeptide may be incubated at a molar ratio in a range of about 1:1 to about 1:200. For example, the molar ratio of the hydrophobic active ingredient verses the polypeptide may be in a range of about 1:1 to about 1:190, about 1:1 to about 1:180, about 1:1 to about 1:170, about 1:1 to about 1:160, about 1:1 to about 1:150, about 1:1 to about 1:140, about 1:1 to about 1:130, about 1:1 to about 1:120, about 1:1 to about 1:110, about 1:1 to about 1:100, about 1:2 to about 1:100, about 1:3 to about 1:100, about 1:4 to about 1:100, about 1:5 to about 1:100, about 1:6 to about 1:100, about 1:7 to about 1:100, about 1:8 to about 1:100, about 1:9 to about 1:100, about 1:10 to about 1:100, about 1:10 to about 1:95, about 1:10 to about 1:90, about 1:10 to about 1:85, about 1:10 to about 1:80, about 1:10 to about 1:75, about 1:10 to about 1:70, about 1:10 to about 1:65, about 1:10 to about 1:60, about 1:10 to about 1:55, about 1:10 to about 1:50, about 1:10 to about 1:45, or about 1:10 to about 1:40.

The polypeptide may be dissolved in a polar solvent. The term "polar solvent" as used herein refers to a solvent consisting of polar molecules. The polar solvent may be a polar aprotic solvent or a polar protic solvent. The polar aprotic solvent may be, for example, dichloromethane, tetrahydrofuran, ethyl acetate, dimethylformamide, acetonitrile, dimethyl sulphoxide, or propylene carbonate. The polar protic solvent may be, for example, formic acid, butanol, isopropanol, n-propanol, ethanol, methanol, acetic acid, nitromethane, or water. The polypeptide may be, for example, dissolved in water.

The hydrophobic active ingredient may be dissolved in a polar solvent. A detailed description of the polar solvent has already been described. The hydrophobic active ingredient may be dissolved in, for example, methanol, ethanol, isopropyl alcohol, butanol, ethylene glycol, propylene glycol, glycerol, acetonitrile, or any combination thereof. The hydrophobic active ingredient may be dissolved in a polar solvent of which a final concentration is in a range of about 10 μM to about 2000 μM, about 50 μM to about 1500 μM, about 100 μM to about 1000 μM, about 100 μM to about 800 μM, about 100 μM to about 600 μM, or about 100 μM to about 400 μM.

According to another aspect of the present invention, a liposome is provided that includes the nanoparticle containing a hydrophobic active ingredient and a polypeptide, and a lipid bilayer, wherein the nanoparticle comprises the hydrophobic active ingredient at a molar ratio in a range of about 0.01 to about 100 with respect to the polypeptide, and the nanoparticle is contained in an interior space of the liposome.

Detailed descriptions of the term hydrophobic, the hydrophobic active ingredient, the polypeptide, the nanoparticle, and the molar ratio of the hydrophobic active material with respect to the polypeptide have already been described.

The term "liposome" as used herein refers to an artificially prepared vesicle composed of a lipid bilayer. A liposome may be a unilamellar vesicle or a multivesicular vesicle.

The nanoparticle containing the hydrophobic active ingredient and the polypeptide may be contained in an interior space of the liposome. Here, the interior space of the liposome may refer to the space encapsulated by the lipid bilayer of the liposome.

The liposome may have an average diameter in a range of about 100 nm to about 5,000 nm, about 150 nm to about 4,800 nm, about 200 nm to about 4,600 nm, about 250 nm to about 4,400 nm, about 300 nm to about 4,200 nm, about 350 nm to about 4,000 nm, about 400 nm to about 3,800 nm, about 450 nm to about 3,600 nm, about 500 nm to about 3,400 nm, about 500 nm to about 3,200 nm, about 500 nm to about 3,000 nm, about 550 nm to about 2,800 nm, about 600 nm to about 2,600 nm, about 650 nm to about 2,400 nm, about 700 nm to about 2,200 nm, about 750 nm to about 2,000 nm, about 800 nm to about 2,000 nm, about 800 nm to about 1,800 nm, about 800 nm to about 1,600 nm, about 800 nm to about 1,400 nm, about 800 nm to about 1,200 nm, about 850 nm to about 1,150 nm, about 900 nm to about 1,100 nm, or about 950 nm to about 1,050 nm. The liposome may have a diameter in average of about 1,000 nm.

The liposome may be a stimulus-sensitive liposome that releases material encapsulated therein in response to a particular stimulus, thereby providing a controlled release. The stimulus-sensitive liposome may be, for example, a temperature-sensitive liposome, a pH-sensitive liposome, a chemical-sensitive liposome, a radiation-sensitive liposome, an ultrasound-sensitive liposome, or any combination thereof. The temperature-sensitive liposome, the pH-sensitive liposome, the chemical-sensitive liposome, the radiation-sensitive liposome, and the ultrasound-sensitive liposome may release materials that are encapsulated therein at a certain temperature, a certain pH, the presence of chemical material, radiation conditions, and ultrasound conditions, respectively. The release temperature may be, for example, in a range of about 25° C. to about 70° C., about 25° C. to about 65° C., about 25° C. to about 60° C., about 25° C. to about 55° C., about 25° C. to about 50° C., about 30° C. to about 50° C., about 35° C. to about 50° C., or about 37° C. (body temperature) to about 50° C. The release pH may be greater or smaller than about 5.5, which is the pH of saline solution. The chemical material may be a material that makes tumor cells become more sensitive to effects of chemotherapy. Examples of the chemical material include cyclosporine A, verapamil, biricodar, or any combination thereof. The irradiation may include alpha (α) rays, beta (β) rays, gamma (γ) rays, X-rays, or any combination thereof. The ultrasound is a wave with a frequency greater than an audio frequency ranging from about 16 Hz to about 20 kHz. The ultrasound may be high intensity focused ultrasound (HIFU), and HIFU is an ultrasound involving high-intensity ultrasound energies in one place to create a concentrated focus.

The term "lipid bilayer" as used herein refers to a membrane made of two layers of lipid molecules. The lipid bilayer is a barrier that keeps ions, proteins, and other molecules in an area where they should be, or prevents them from diffusing into an area where they should not be. The "lipid molecules" forming the lipid bilayer may be molecules consisting of a hydrophilic head and a hydrophobic tail. The lipid molecules may each have 14 to 50 carbon atoms.

The lipid bilayer may contain a phospholipid, a lipid conjugated to polyethylene glycol (PEG), cholesterol, or any combination thereof.

A phospholipid is a compound lipid containing a phosphate ester, and is a main component of biological membranes, such as cell membranes, endoplasmic reticulum, mitochondria, and myelin sheath around nerve fibers. Phospholipids include a hydrophilic head and two hydrophobic tails. When the phospholipids are exposed to water, they arrange themselves into a two-layered sheet (a bilayer) with all of their tails pointing toward the center of the sheet. The center of this bilayer contains almost no water and also excludes molecules such as sugars or salts that dissolve in water but not in oil. The phospholipid may include phosphatidic acid, phosphatidylethanolamine, phosphatidylcholine, phosphatidylserine, phosphatidylinositol, phosphosphingolipid, or any combination thereof. Phosphatidylcholine (PC) may include choline as a head group and glycerophosphoric acid as a tail, wherein glycerophosphoric acid may be saturated fatty acid or unsaturated fatty acid and have 14 to 50 carbon atoms. Examples of the PC include 1,2-dierucoyl-sn-glycero-3-phosphocholine (DEPC), 1,2-distearoyl-sn-glycero-3-phosphocholine (DSPC), 1,2-dipalmitoyl-sn-glycero-3-phosphocholine (DPPC), egg PC, soy bean PC, or any combination thereof.

The lipid conjugated to PEG may be, for example, phosphatidylethanolamine (PE)-PEG. The PE may be saturated fatty acid, unsaturated fatty acid, mixed acyl chain, lysophosphatidylethanolamine, or any combination thereof. The lipid conjugated to PEG may be, for example, 1,2-distearoylphosphatidylethanolamine-methyl-polyethylene glycol (DSPE-PEG).

The term "cholesterol" as used herein encompasses cholesterol and cholesterol derivatives, such as sitosterol, ergosterol, stigmasterol, 4,22-stigmastadiene-3-on, stigmasterol acetate, lanosterol, cycloartenol, or any combination thereof. Cholesterol may enhance fluidity of a lipid bilayer and lower the permeability of the lipid bilayer.

According to another aspect of the present invention, pharmaceutical composition for delivering a hydrophobic active ingredient to a subject includes a liposome including a nanoparticle which contains a hydrophobic active ingredient and a polypeptide, and a lipid bilayer, wherein the nanoparticle includes the hydrophobic active ingredient at a molar ratio in a range of about 0.01:1 to about 100:1 with respect to the polypeptide, and the nanoparticle is contained in an interior space of the liposome.

Detailed descriptions of the term "hydrophobic", the hydrophobic active ingredient, the polypeptide, the nanoparticle, the molar ratio of the hydrophobic active ingredient with respect to the polypeptide, the lipid bilayer, the interior space, and the liposome have already been described.

The pharmaceutical composition may further include a pharmaceutically acceptable carrier or diluent. The pharmaceutically acceptable carrier or diluent may be known in the art. Examples of the pharmaceutically acceptable carrier or diluents include lactose, dextrose, sucrose, sorbitol, mannitol, starch, acacia gum, calcium phosphate, alginate, gelatin, calcium silicate, microcrystalline cellulose, polyvinylpyrrolidone, cellulose, water (for example, saline or sterile water), syrup, methyl cellulose, methylhydroxybenzoate, propylhydroxybenzoate, talc, magnesium stearate, mineral oil, Ringer's solution, buffer, maltodextrin solution, glycerol, ethanol, or any combination thereof. The pharmaceutical composition may further include a lubricant, a wetting agent, a sweetening agent, a flavoring agent, an emulsifier, a suspending agent, a preserving agent, or any combination thereof.

According to methods that are known in the art, the pharmaceutical composition may be formulated and prepared in the form of a unit dose using the pharmaceutically acceptable carrier and/or diluents, or may be introduced and prepared in a multi-dose container. Here, the pharmaceutical composition may be formulated as a solution of oil or aqueous medium, suspension, syrup, or emulsion. In some embodiments, the pharmaceutical composition may be formulated as extracts, powders, powdered drugs, granules, tablets, or capsules. The pharmaceutical composition may further include a dispersant or a stabilizer. The aqueous medium may contain physiological saline or PBS.

According to another aspect of the present invention, a method of delivering a hydrophobic active ingredient to a target site in the body of a subject includes administrating a pharmaceutical composition including a liposome including a nanoparticle which contains a hydrophobic active ingredient and a polypeptide, and a lipid bilayer to a subject, wherein the hydrophobic active ingredient is contained at a molar ratio in a range of about 0.01:1 to about 100:1 with respect to the polypeptide, and the nanoparticle is contained in an interior space of the liposome; and applying a stimulus to the target site of the subject to release the nanoparticle.

The method includes administrating of the pharmaceutical composition comprising a liposome comprising a nanoparticle which comprises a hydrophobic active ingredient and a polypeptide, and a lipid bilayer to the subject, wherein the nanoparticle includes the hydrophobic active ingredient at a molar ratio in a range of about 0.01:1 to about 100:1 with respect to the polypeptide, and the nanoparticle is contained in an interior space of the liposome.

Detailed description of the term "hydrophobic", the hydrophobic active ingredient, the polypeptide, the nanoparticle, the molar ratio of the nanoparticle, the lipid bilayer, the interior space, the liposome, and the pharmaceutical composition have already been described.

The subject may be mammals including rats, mice, cattle, and humans.

The pharmaceutical composition may be administrated into mammals including rats, mice, cattle, and humans by various routes. The administration may, for example, oral administration or rectal or intravenous injection, intramuscular injection, intradermal injection, intrauterine durameter or intracerebroventricular injection.

The administration may be oral administration or parenteral administration. The parenteral administration may be, for example, intravenous, intradermal, intramuscular, intracavity (abdominal cavity, joints, or eye) or direct injection. The direct injection may involve injecting directly into a diseased site such as a tumor site. The liposome may be administered intravenously and accordingly brought to the target site such as a tumor site by blood flow. Dosage of the liposome may be prescribed according to various factors such as formulation methods, administration methods, patient's age, weight, gender and morbidity, foods, administration times, administration routes, excretion rates, and reaction sensitivity. Dosage of the liposome may be in a range of about 0.001 mg/kg to about 100 mg/kg.

The method also includes applying of the stimulus to the target site of the subject to release the nanoparticle.

A detailed description of the subject has already been described.

The stimulus may be heating, pH variation, drug administration, irradiation, ultrasound, or any combination thereof. The heating may rise a temperature, for example, to a range from about 25° C. to about 70° C., about 25° C. to about 65° C., about 25° C. to about 60° C., about 25° C. to about 55° C., about 25° C. to about 50° C., about 30° C. to about 50° C., about 35° C. to about 50° C., or about 37° C. (body temperature) to about 50° C. The pH may be greater or smaller than about 5.5, which is the pH of saline solution. The heating may be performed, for example, for about 1 second to about 48 hours, about 1 minute to about 36hours, about 5 minutes to about 24 hours, about 10 minutes to about 24 hours, about 30 minutes to about 12 hours, or about 1 hour to about 6 hours. Detailed descriptions of the irradiation and the ultrasound have already been described. The ultrasound may be HIFU, and HIFU may have a frequency, for example, in a range of about 20 kHz to about 2.0 MHz, about 40 kHz to about 2.0 MHz, about 60 kHz to about 2.0 MHz, about 80 kHz to about 2.0 MHz, about 100 kHz to about 2.0 MHz, about 150 kHz to about 2.0 MHz, about 200 kHz to about 2.0 MHz, about 250 kHz to about 2.0 MHz, about 300 kHz to about 2.0 MHz, about 350 kHz to about 2.0 MHz, about 400 kHz to about 2.0 MHz, about 450 kHz to about 2.0 MHz, about 500 kHz to about 2.0 MHz, about 550 kHz to about 2.0 MHz, about 600 kHz to about 2.0 MHz, about 650 kHz to about 2.0 MHz, about 700 kHz to about 2.0 MHz, about 750 kHz to about 2.0 MHz, about 800 kHz to about 2.0 MHz, about 850 kHz to about 2.0 MHz, about 900 kHz to about 2.0 MHz, about 950 kHz to about 2.0 MHz, about 1.0 MHz to about 2.0 MHz, about 1.1 MHz to about 1.9 MHz, about 1.2 MHz to about 1.8 MHz, about 1.3 MHz to about 1.7 MHz, or about 1.4 MHz to about 1.6 MHz. For example, HIFU may have a frequency of about 1.5 MHz.

In response to the stimulus, the nanoparticles containing the hydrophobic active ingredient and the polypeptide may be released from the liposome.

The method may further include preventing and treating disease by releasing the nanoparticles containing the hydrophobic active ingredient and the polypeptide from the liposome. The term "prevention" as used herein refers to inhibition of disease occurrence. The term "treatment" as used herein refers to suppression, reduction, or elimination of disease development. The disease may be cancer. The released nanoparticles containing the hydrophobic active ingredient and the polypeptide may be absorbed into cells in the target site, and accordingly the polypeptide may be degraded by intracellular enzymes. When the polypeptide is degraded, the hydrophobic active ingredient is released so as to exhibit its activity.

According to the nanoparticle containing the hydrophobic active ingredient and the polypeptide, the method of manufacturing the nanoparticle, and the use of the nanoparticle, the nanoparticle may be simply manufactured without adding a chemical additive. Also, there may be no interaction between the lipid and the hydrophobic active ingredient, and drugs may be efficiently released and non-invasively delivered to the target site of the subject so as to minimize side effects on normal tissue.

Hereinafter, one or more embodiments of the present invention will now be described more fully with reference to the following examples. However, these examples are provided only for illustrative purposes and are not intended to limit the scope of the present invention.

EXAMPLE 1

Preparation of Nanoparticles Including Sorafenib and Albumin and Measurement of Sizes of the Prepared Nanoparticles Bovine serum albumin (BSA) (Sigma Aldrich) was dissolved in distilled water to prepare a BSA solution in concentration of 0.01 mM. Next, sorafenib (SRF) (Santa Cruz Biotechnology, Inc.) was dissolved in an ethanol to prepare a SRF solution in concentration of 10 mM.

The BSA solution was mixed with the SRF solution so as to prepare a mixed solution of which a concentration ratio of BSA versus SRF was 1:1, 1:2, 1:5, 1:10, 1:20, or 1:40. The mixed solution was then incubated at room temperature for 10 minutes to prepare nanoparticles containing SRF and albumin.

Figure 1B:
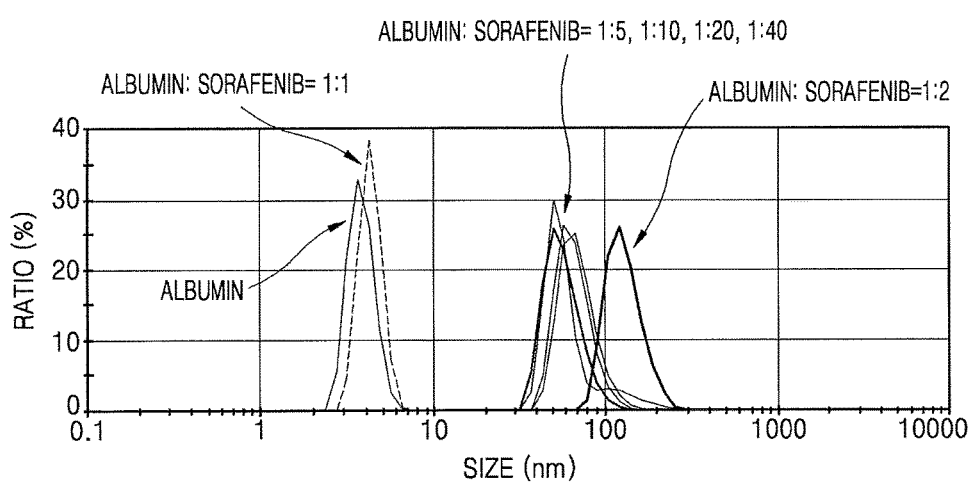
FIG. 1B is a graph showing sizes of nanoparticles including SRF and BSA by using a dynamic light scattering (DLS) analyzer.

The sizes of the prepared nanoparticles were measured by using a dynamic light scattering (DLS) analyzer (Malvern Instruments Ltd), and the results were shown in FIG. 1B.

Referring to FIG. 1B, if the concentration ratio of SRF versus BSA was 1:1, the size of the prepared nanoparticles was not significantly different from that of BSA. However, if the concentration ratio of SRF versus BSA was greater than 1:1, the size of the prepared nanoparticles was significantly increased. Therefore, it was confirmed that there have been prepared nanoparticles having a diameter of about 100 nm.

Figure 1C:
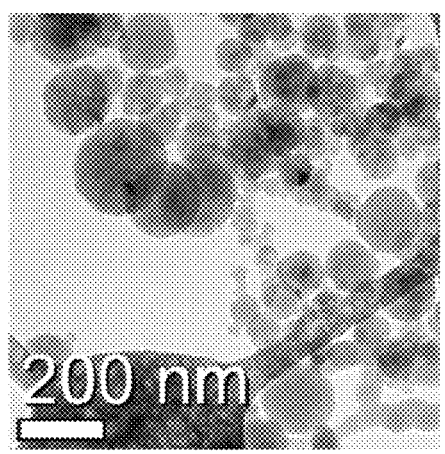
FIG. 1C is a transmission electron microscope (TEM) image showing nanoparticles including SRF and BSA.
Figure 1D:
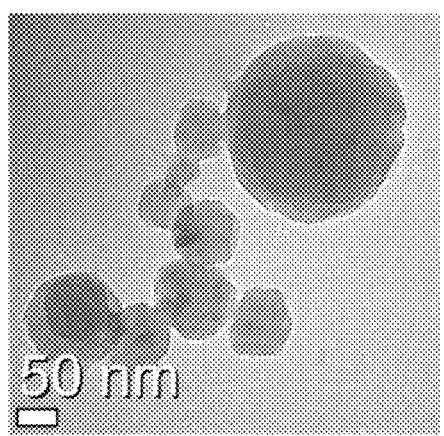
FIG. 1D is an enlarged view of the image of FIG. 1C.

Meanwhile, the shape of the prepared nanoparticles of which a concentration ratio of SRF versus BSA was 1:2 was confirmed by using a transmission electron microscope (TEM). In detail, the prepared nanoparticles were observed after being loaded into Holey carbon film-supported grids. The grids were then dipped in liquid nitrogen and transferred to a cyotransfer holder (Gatan). Images were obtained by using a Tecnai F20 field emission gun electronic microscope equipped with a CCD camera (2k, Gatan) that operates at 200 kV (FEI). The obtained images were shown in FIGS. 1C and 1D. Referring to FIGS. 1C and 1D, it was confirmed that there have been prepared nanoparticles.

EXAMPLE 2

Molar Ratio of SRF Versus BSA in the Nanoparticles Containing SRF and BSA

The molar ratio of SRF versus BSA in the nanoparticles prepared according to Example 1 was measured.

The nanoparticles of Example 1 were put into a centrifugal filter (having 30 KDa molecular weight cut-off), and then centrifuged at a temperature of 4° C. for 10 minutes at a speed of 16,000×g so as to remove SRF that was not bound to BSA.

Figure 2:
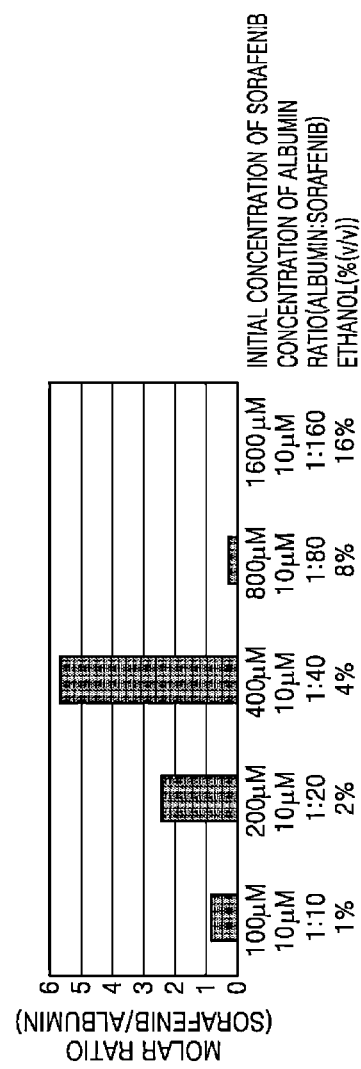
FIG. 2 is a graph showing molar ratios of SRF versus BSA in nanoparticles including SRF and BSA.

In order to measure the molar ratio of SRF in the purified nanoparticles, acetonitrile (FISHER) was added to the purified nanoparticles so as to prepare a reactant of which a volume ratio of supernatant versus acetonitrile was 3:7. The reactant was then incubated at a temperature of 25° C. for 3 minutes to dissociate SRF from the nanoparticles. Next, the reactant was centrifuged at a temperature of 4° C. for 10 minutes at a speed of 13,000×g to remove pellets including BSA. Then, the supernatant was subject to high performance liquid chromatography (HPLC) (Waters e2695, Column: Shiseido C18 CAPCELL PAK 4.6 mml.D.×250 nm) to quantify SRF. The molar ratio of SRF versus BSA was calculated, and the results were shown in FIG. 2 (y-axis: molar ratio of SRF versus BSA). In FIG. 2, the concentration of ethanol (%(v/v)) is the concentration of ethanol in water.

Referring FIG. 2, it was confirmed that if the molar ratio of BSA versus SRF was 1:40 or less than 1:40 on the basis of the initial concentration measured during the preparation of the nanoparticles, the molar ratio of SRF was increased in the nanoparticles. If the molar ratio of BSA versus SRF was 1:80 or greater than 1:80, the molar ratio of SRF was decreased in the nanoparticles.

EXAMPLE 3

Confirmation on Effects of Solvent, Hydrophobic Material, and Concentration Ratio of Hydrophobic Materials and BSA in Preparation of Nanoparticles It was confirmed whether kinds of hydrophobic materials or solvents affect the preparation of nanoparticles. It was also confirmed whether a concentration ratio of hydrophobic materials and BSA affects the preparation of nanoparticles.

As hydrophobic materials, sorafenib (Santa Cruz Biotechnology, Inc.), docetaxel (Aldrich), and nile red (Aldrich) were prepared. Each of the hydrophobic materials was dissolved in ethanol, methanol, 2-propanol, or acetonitrile.

The reactant was then mixed with 0.01 mM BSA (in distilled water) so as to a concentration ratio of the hydrophobic materials versus BSA was 1:4 or 1:16. Next, the mixed solution was incubated at room temperature for 10 minutes to prepare nanoparticles containing hydrophobic materials and BSA.

Figure 3:
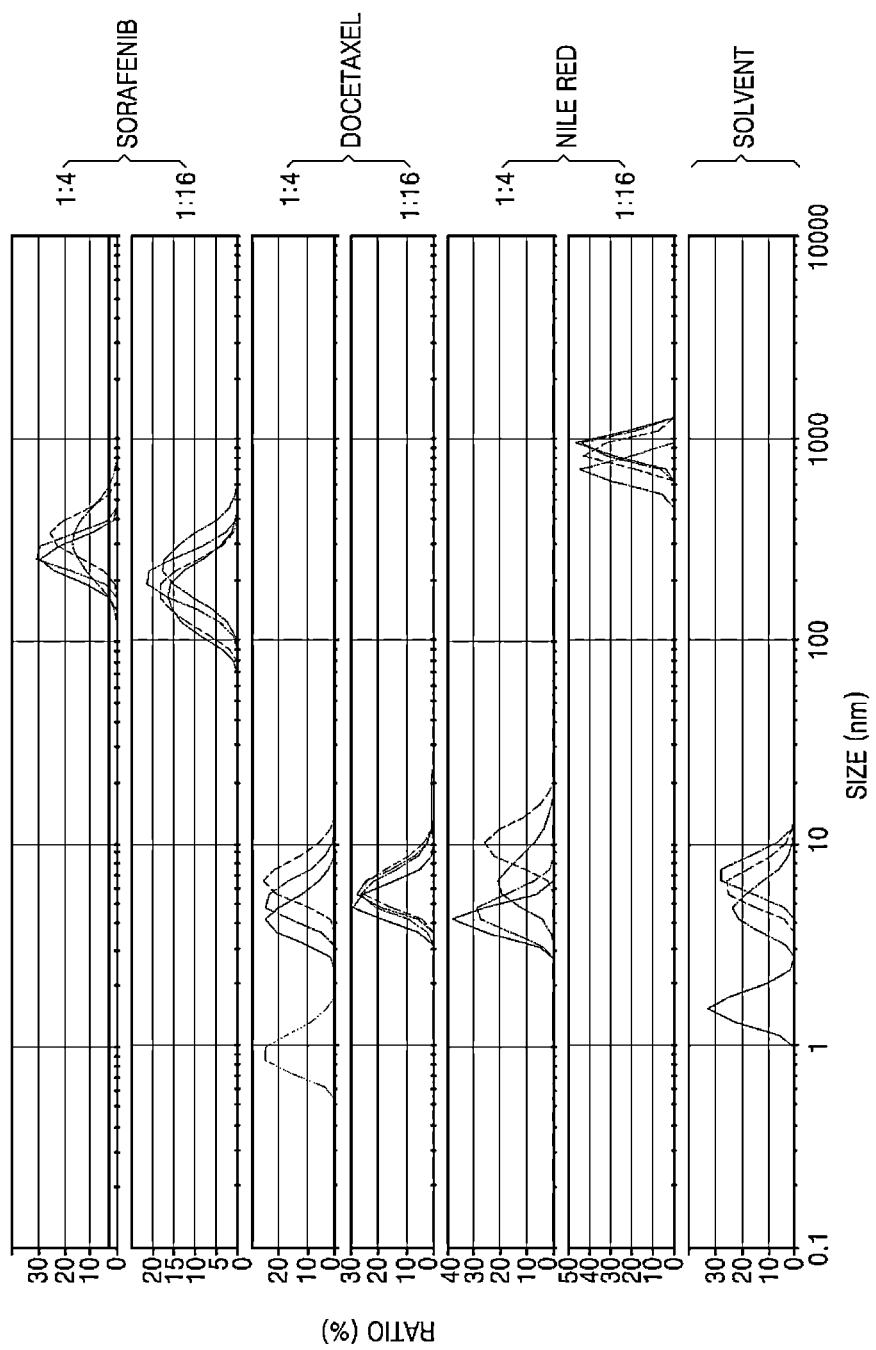
FIG. 3 is a graph showing sizes of nanoparticles including hydrophobic materials and BSA by using a DLS analyzer (———: acetonitrile, – - – ·: ethanol, — - - —: 2-propanol, — — — —: methanol)

The sizes of the prepared nanoparticles were measured by using a DLS analyzer (Malvern Instruments Ltd), and the results were shown in FIG. 3 (———: acetonitrile, — - — - : ethanol, — - - —: 2-propanol, — — — —: methanol).

Referring to FIG. 3, it was confirmed that the preparation of the nanoparticles was less affected by the kinds of the solvent dissolving the hydrophobic material. However, it was confirmed that the preparation of the nanoparticles was affected by the properties of the hydrophobic material itself and by the molar ratio of the hydrophobic material versus BSA.

EXAMPLE 4

Preparation Of Liposomes Including Nanoparticles Containing SRF and BSA and Measurement of Sizes of Prepared Liposomes Nanoparticles containing SRF and BSA were prepared by adding phosphate buffered saline (PBS) to the nanoparticles of Example 1, wherein PBS was added to volumes corresponding to 60 mg of BSA of the nanoparticles per 1 ml of PBS.

Liposomes were prepared in the form of unilamellar vesicles by mixing 1,2-dierucoyl-sn-glycero-3-phosphocholine (DEPC), 1,2-distearoyl-sn-glycero-3-phosphocholine (DSPC), cholesterol, and [1,2-distearoyl-sn-glycero-3-phosphoethanolamine-N-[methoxy(polyethylene glycol)-2000] (ammonium salt) (DSPE-PEG] at a molar ratio of 52:5:35:8.

In detail, SA-V3-NH$_2$ (Peptron, Inc.) was dissolved in an ethanol, and DEPC (Avanti Polar lipids, Inc.), DSPC (Avanti Polar lipids, Inc.), cholesterol (Avanti Polar lipids, Inc.), and DSPE-PEG (Avanti Polar lipids, Inc.) were dissolved in a chloroform. The ethanol and the chloroform were mixed in a round bottom flask, and the solvents therein were evaporated at room temperature by using a rotary evaporator, thereby preparing a lipid thin film on the inner wall of the round bottom flask.

1 ml of the nanoparticles including SRF and BSA were added to the round bottom flask at room temperature so as to hydrate the lipid thin film. The hydrated solution was then subject to vortexing. The liposomes were centrifuged at a temperature of 4° C. for 10 minutes at a speed of 1,000×g. The supernatant was removed so as to remove the nanoparticles that were not contained in the liposomes. The pellets were re-suspended with PBS. The sizes of the prepared liposomes were measured by using a DLS analyzer (Malvern Instruments Ltd), and the results were shown in FIG. 4.

Figure 4:
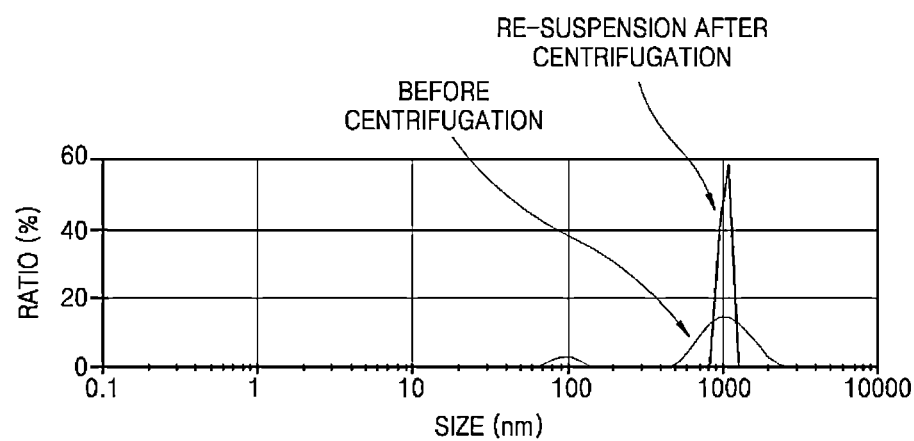
FIG. 4 is a graph showing sizes of liposomes by using a DLS analyzer according.

Referring to FIG. 4, it was confirmed that there have been prepared liposomes having a uniform size (a diameter of about 1 μm).

EXAMPLE 5

Destruction of Liposomes Including Nanoparticles Containing SRF and BSA by Using Ultrasound The liposomes of Example 4 were sonicated at a temperature of 25° C. for 0 second (control group), 0.5 minutes, 2 minutes, 5 minutes, or 10 minutes by using a pool-type sonicator (Branson).

Figure 5:
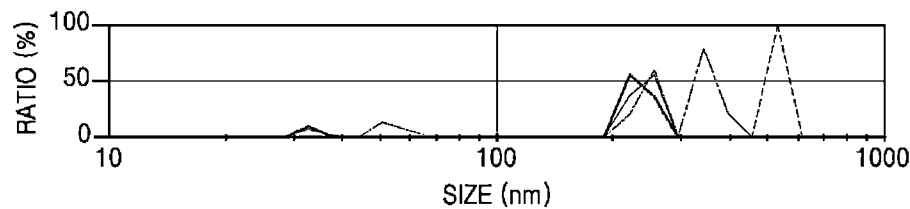
FIG. 5 is a graph showing sizes of liposomes by using a DLS analyzer after being sonicated (- - - -·: 2 minutes, ———: 5 minutes, – - – -: 10 minutes, — - - —: 0.5 minutes, — — — —: untreated).

The sizes of the reactants were measured by using a DLS analyzer (Malvern Instruments Ltd), and the results were shown in FIG. 5 (- - - -: : 2 minutes, ———: 5 minutes, — - — -: 10 minutes, — - - -—: 0.5 minutes, — — — —: untreated).

Referring to FIG. 5, the sizes of the liposomes that were not sonicated were in a range of about 460 nm to about 620 nm, and the sizes of the liposomes that were sonicated for at least 2 minutes were decreased to a range from about 200 nm to about 300 nm. Thus, it was deemed that the nanoparticles containing SRF and BSA were released from the liposomes by the sonication, and accordingly the sizes of the liposomes were decreased.

EXAMPLE 6

Confirmation of Release of Nanoparticles Containing SRF and BSA by Ultrasound

The liposomes of Example 4 were sonicated by using a probe-type sonicator (Sonics and materials, Inc., VCX130) at a temperature of 4° C. for 2 minutes. Here, the sonication was performed at amplitude of 50% by repeating an on/off cycle each for 1 second/1 second.

The reactants were subject to enzyme-linked immunospecific assay (ELISA) using anti-BSA antibodies (Koma biotech) to quantify BSA released from the liposomes. TRITON X-100® (Aldrich) was added to the liposomes of Example 4 to dissociate liposomes, and the solution having the dissociated liposomes was used as a positive control group. The concentrations of the quantified BSA wereshown in FIG. 6 (1: a solution dissolving liposomes including nanoparticles containing SRF and BSA were dissociated, 2: liposomes that were not sonicated, 3: liposomes that were sonicated for 2 minutes).

Figure 6:
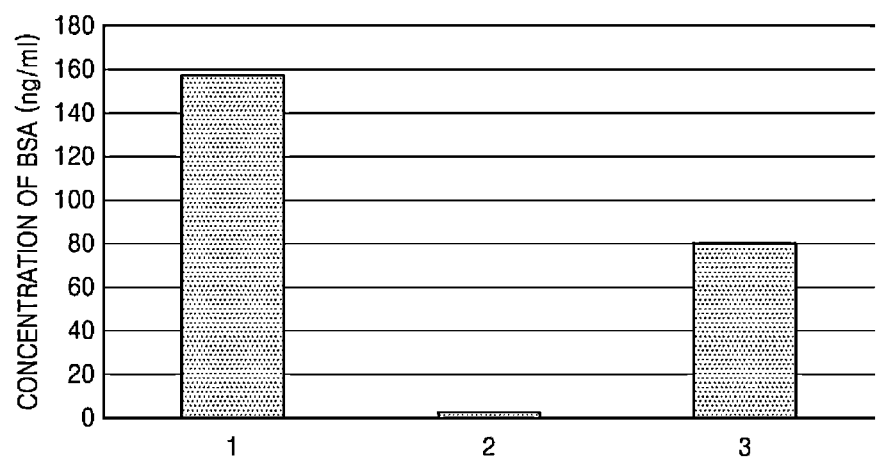
FIG. 6 is a graph showing results of ELISA that quantifies concentrations of BSA released from liposomes (1: a solution dissolving liposomes including nanoparticles containing SRF and BSA, 2: liposomes that were not sonicated, 3: liposomes that were sonicated for 2 minutes).

Referring to FIG. 6, if the amount of BSA contained in the liposomes including the nanoparticles was set to 100%, 2% of the BSA were released from the liposomes that were not sonicated, and 51% of the BSA were released from the liposomes that were sonicated for 2 minutes. Therefore, it was confirmed that the nanoparticles containing SRF and BSA were released from the liposomes by ultrasound.

EXAMPLE 7

Confirmation of Cytotoxicity by the Released Nanoparticles Containing SRF and BSA Liposomes that were sonicated were incubated with cells to confirm the cell viability.

The liposomes of Example 4 were sonicated at a temperature of 25° C. for 16 minutes by using a pool-type sonicator (Branson).

The sonicated liposomes, unsonicated liposomes, 50 μM of SRF (Santa Cruz Biotechnology, Inc.) dissolved in dimethyl sulfoxide (DMSO) (Aldrich), or DMSO itself was added to about 5,000 HepG2 liver cancer cells, followed by being incubated at a temperature of 37° C. for 3 hours. Here, the medium used in the incubation was exchanged with fresh medium. The cells were incubated for at a temperature of 37° C. for 3 days, and number of the cells was counted by using a CCK-8 kit (Dojindo). The cell viability was relatively calculated with respect to the number of the cells that were treated with DMSO, and the results were shown in FIG. 7 (1: DMSO, 2: SRF dissolved in DMSO, 3: liposomes that are not sonicated, 4: liposomes that are sonicated for 16 minutes).

Figure 7:
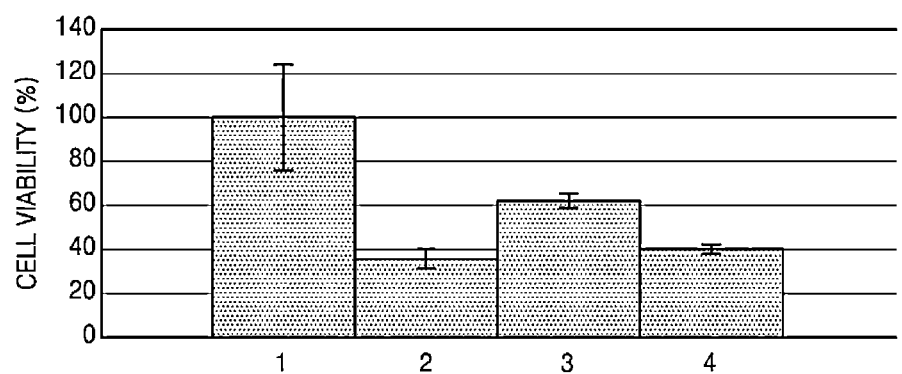
FIG. 7 is a graph showing cell viability (%) by nanoparticles including hydrophobic materials and BSA that are released (1: dimethyl sulfoxide (DMSO), 2: SRF dissolved in DMSO, 3: liposomes that are not sonicated, 4: liposomes that are sonicated for 16 minutes).

Referring to FIG. 7, the cell viability in the liposomes that were sonicated for 16 minutes was about 40%, which was at a similar level with the cell viability in the SRF dissolved in DMSO (about 36%). The cell viability in the liposomes that were not sonicated was about 62%, and that is, some of the liposomes may be introduced into the cells during the incubation that was performed at a temperature of 37° C. for 3 hours, or the nanoparticles may be leaked from the liposomes.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A nanoparticle consisting of at least one hydrophobic active ingredient and at least one polypeptide, wherein the molar ratio of the hydrophobic active ingredient to the polypeptide is about 0.01:1 to about 100:1, and the nanoparticle has an average diameter of 10 nm to 100 nm.

2. The nanoparticle of claim 1, wherein the at least one hydrophobic active ingredient comprises a hydrophobic drug, an imaging agent, or a combination thereof.

3. The nanoparticle of claim 2, wherein the at least one hydrophobic active ingredient comprises sorafenib, paclitaxel, docetaxel, doxorubicin, cyclosporine A, amphothericin B, indinavir, rapamycin, coenzyme Q10, ursodeoxycholic acid, ilaprazole, imatinib mesilate, tanespimycin, or a combination thereof.

4. The nanoparticle of claim 1, wherein the at least one polypeptide comprises albumin, transferrin, apolipoprotein, a fragment thereof, or a combination thereof.

5. The nanoparticle of claim 1, wherein the molar ratio of the at least one hydrophobic active ingredient to the at least one polypeptide is about 5:1 to about 40:1.

6. The nanoparticle of claim 1, wherein the nanoparticle has an average diameter of 30 nm to 100 nm.

7. A method of manufacturing a nanoparticle, the method comprising:
  incubating at least one hydrophobic active ingredient and at least one polypeptide to prepare a nanoparticle,
  wherein the nanoparticle consists of the at least one hydrophobic active ingredient and the at least one polypeptide, the at least one hydrophobic active ingredient is contained at a molar ratio in a range of about 0.01:1 to about 100:1 with respect to the at least one polypeptide, and the nanoparticle has an average diameter of 10 nm to 100 nm, wherein the hydrophobic active ingredient is dissolved in a polar solvent and the polar solvent comprises methanol, ethanol, isopropyl alcohol, butanol, ethylene glycol, propylene glycol, glycerol, acetonitrile, or a combination thereof.

8. The method of claim 7, wherein the at least one hydrophobic active ingredient and the at least one polypeptide are incubated at a molar ratio of about 1:1 to about 1:200.

9. The method of claim 7, wherein the at least one polypeptide is dissolved in a polar solvent.

10. The method of claim 9, wherein the polar solvent is water.

11. The method of claim 7, wherein the at least one hydrophobic active ingredient is dissolved in a polar solvent at a final concentration of about 10 µM to about 2000 µM.

12. A liposome comprising:
  the nanoparticle of claim 1 and a lipid bilayer,
  wherein the nanoparticle is contained in an interior space of the liposome.

13. The liposome of claim 12, wherein the liposome has an average diameter of about 100 to about 5,000 nm.

14. The liposome of claim 12, wherein the liposome is sensitive to a stimulus.

15. The liposome of claim 14, wherein the stimulus is temperature, pH, a chemical, radiation, ultrasound, or a combination thereof.

16. The liposome of claim 12, wherein the lipid bilayer comprises a phospholipid, a lipid conjugated to polyethylene glycol, cholesterol, or a combination thereof.

17. A pharmaceutical composition comprising the liposome of claim 12.

18. A method of delivering a hydrophobic active ingredient to a target site in a subject, the method comprising:
  administering the pharmaceutical composition of claim 17 to a subject; and
  applying a stimulus to a target site in the subject to release the nanoparticle, whereby the hydrophobic active ingredient is delivered to the target site in the subject.

* * * * *